(12) United States Patent
Angel

(10) Patent No.: US 9,655,753 B2
(45) Date of Patent: May 23, 2017

(54) STENT DELIVERY SYSTEM AND METHOD OF USE

(75) Inventor: Luis F. Angel, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 635 days.

(21) Appl. No.: 10/529,798

(22) PCT Filed: Sep. 30, 2003

(86) PCT No.: PCT/US03/30844
§ 371 (c)(1),
(2), (4) Date: Oct. 28, 2005

(87) PCT Pub. No.: WO2004/030571
PCT Pub. Date: Apr. 15, 2004

(65) Prior Publication Data
US 2006/0184224 A1    Aug. 17, 2006

Related U.S. Application Data

(60) Provisional application No. 60/414,770, filed on Sep. 30, 2002.

(51) Int. Cl.
*A61F 2/04* (2013.01)
*A61F 2/95* (2013.01)
(Continued)

(52) U.S. Cl.
CPC .............. *A61F 2/95* (2013.01); *A61F 2/966* (2013.01); *A61B 1/2676* (2013.01); *A61F 2/04* (2013.01);
(Continued)

(58) Field of Classification Search
CPC .................. A61F 2/04; A61F 2002/043; A61F 2002/9517; A61F 2002/9522; A61B 17/24; A61B 2017/242
(Continued)

(56) References Cited

U.S. PATENT DOCUMENTS

| 3,616,799 | A | 11/1971 | Sparks |
| 3,709,227 | A | 1/1973 | Hayward |

(Continued)

FOREIGN PATENT DOCUMENTS

| DE | 9409161 | 7/1995 |
| GB | 2348138 | 9/2000 |

(Continued)

OTHER PUBLICATIONS

AA01—International Search Report and Written Opinion for PCT/US04/27285 mailed Jul. 20, 2005.

(Continued)

*Primary Examiner* — Diane Yabut
(74) *Attorney, Agent, or Firm* — Stoel Rives LLP

(57) ABSTRACT

A stent delivery system may be used to position a stent in a body lumen. An endoscope may be positionable in the stent delivery system facilitating direct visual observation during placement of the stent. The stent delivery system may include a first conduit, wherein the endoscope is positionable. A second conduit, wherein the first conduit is positionable, may function to releasably position the stent in the body lumen during use. The stent delivery system may include a lock that functions to inhibit movement of the first conduit relative to the second conduit during use. Retraction of the distal end of the second conduit, relative to the first conduit and the stent, may deploy the stent in a body lumen. Indicia, visibly positioned on the proximal end of the stent delivery system, may function to facilitate determination of an extent of deployment of the stent during use.

28 Claims, 4 Drawing Sheets

(51) Int. Cl.
*A61F 2/966* (2013.01)
*A61B 1/267* (2006.01)

(52) U.S. Cl.
CPC . *A61F 2002/043* (2013.01); *A61F 2002/9517* (2013.01)

(58) Field of Classification Search
USPC .................. 623/1.11, 1.23, 9; 606/194, 108
See application file for complete search history.

(56) References Cited

U.S. PATENT DOCUMENTS

| | | | |
|---|---|---|---|
| 3,769,983 A | 11/1973 | Merav | |
| 3,995,643 A | 12/1976 | Merav | |
| 4,665,918 A * | 5/1987 | Garza et al. | 623/1.11 |
| 4,987,895 A | 1/1991 | Heimlich | |
| 4,990,151 A | 2/1991 | Wallsten | |
| 5,026,377 A | 6/1991 | Burton et al. | |
| 5,143,062 A | 9/1992 | Peckham | |
| 5,201,757 A * | 4/1993 | Heyn et al. | 606/198 |
| 5,250,059 A * | 10/1993 | Andreas et al. | 606/159 |
| 5,512,055 A | 4/1996 | Domb et al. | |
| 5,762,638 A | 6/1998 | Shikani et al. | |
| 5,776,142 A * | 7/1998 | Gunderson | 623/1.11 |
| 5,782,838 A | 7/1998 | Beyar et al. | |
| 5,791,341 A | 8/1998 | Bullard | |
| 5,803,080 A | 9/1998 | Freitag | |
| 5,817,102 A | 10/1998 | Johnson et al. | |
| 5,830,179 A | 11/1998 | Mikus et al. | |
| 5,893,868 A | 4/1999 | Hanson et al. | |
| 5,938,623 A * | 8/1999 | Quiachon et al. | 600/585 |
| 6,071,287 A | 6/2000 | Verbeek | |
| 6,093,194 A * | 7/2000 | Mikus et al. | 606/108 |
| 6,146,389 A | 11/2000 | Geitz | |
| 6,221,081 B1 | 4/2001 | Mikus et al. | |
| 6,344,044 B1 | 2/2002 | Fulkerson et al. | |
| 6,368,344 B1 * | 4/2002 | Fitz | 623/1.11 |
| 6,391,050 B1 | 5/2002 | Broome | |
| 6,520,983 B1 * | 2/2003 | Colgan et al. | 623/1.11 |
| 6,585,639 B1 | 7/2003 | Kotmel et al. | |
| 6,629,981 B2 * | 10/2003 | Bui et al. | 606/108 |
| 6,692,494 B1 | 2/2004 | Cooper et al. | |
| 2002/0007222 A1 | 1/2002 | Desai | |
| 2003/0114912 A1 * | 6/2003 | Sequin et al. | 623/1.11 |
| 2003/0215564 A1 * | 11/2003 | Heller et al. | 427/2.25 |
| 2004/0093063 A1 * | 5/2004 | Wright et al. | 623/1.12 |
| 2005/0205097 A1 | 9/2005 | Kyle, Jr. | |
| 2007/0055343 A1 | 3/2007 | Angel | |

FOREIGN PATENT DOCUMENTS

| | | | |
|---|---|---|---|
| GB | 2348138 A * | 9/2000 | |
| JP | 10-243916 | 9/1998 | |
| JP | 2002-224021 | 8/2002 | |
| JP | 2002-238840 | 8/2002 | |
| JP | 2002253562 | 9/2002 | |
| JP | 2002253563 | 9/2002 | |
| WO | 2004030571 | 4/2004 | |
| WO | 2005018713 | 3/2005 | |

OTHER PUBLICATIONS

AA02—International Search Report for PCT/US03/30844 mailed Mar. 2, 2004.
AA03—Written Opinion for PCT/US03/30844 mailed Aug. 12, 2004.
AA04—International Preliminary Examination Report for PCT/US03/30844 mailed Jan. 10, 2005.
Office Action issued on Jun. 29, 2011 for European Counterpart Application No. 03 77 4506.
Office Action issued on Dec. 1, 2008 for Australian Counterpart Application No. 2003282886.
Office Action issued on Oct. 13, 2009 for Japanese Counterpart Application No. 2004-541907.
Office Action issued on Jun. 29, 2010 for Japanese Counterpart Application No. 2004-541907.
Office Action issued on Apr. 29, 2010 for Canadian Counterpart Application No. 2,499,710.
Office Action issued on Feb. 18, 2011 for Canadian Counterpart Application No. 2,499,710.
Search Report issued on Mar. 25, 2011 for European Counterpart Application No. 03 77 4506.
Office Action issued on Dec. 16, 2010 for Australian Counterpart Application No. 2009202556.
Examiners First Report for Application No. AU2003282886 mailed Sep. 26, 2007.

* cited by examiner

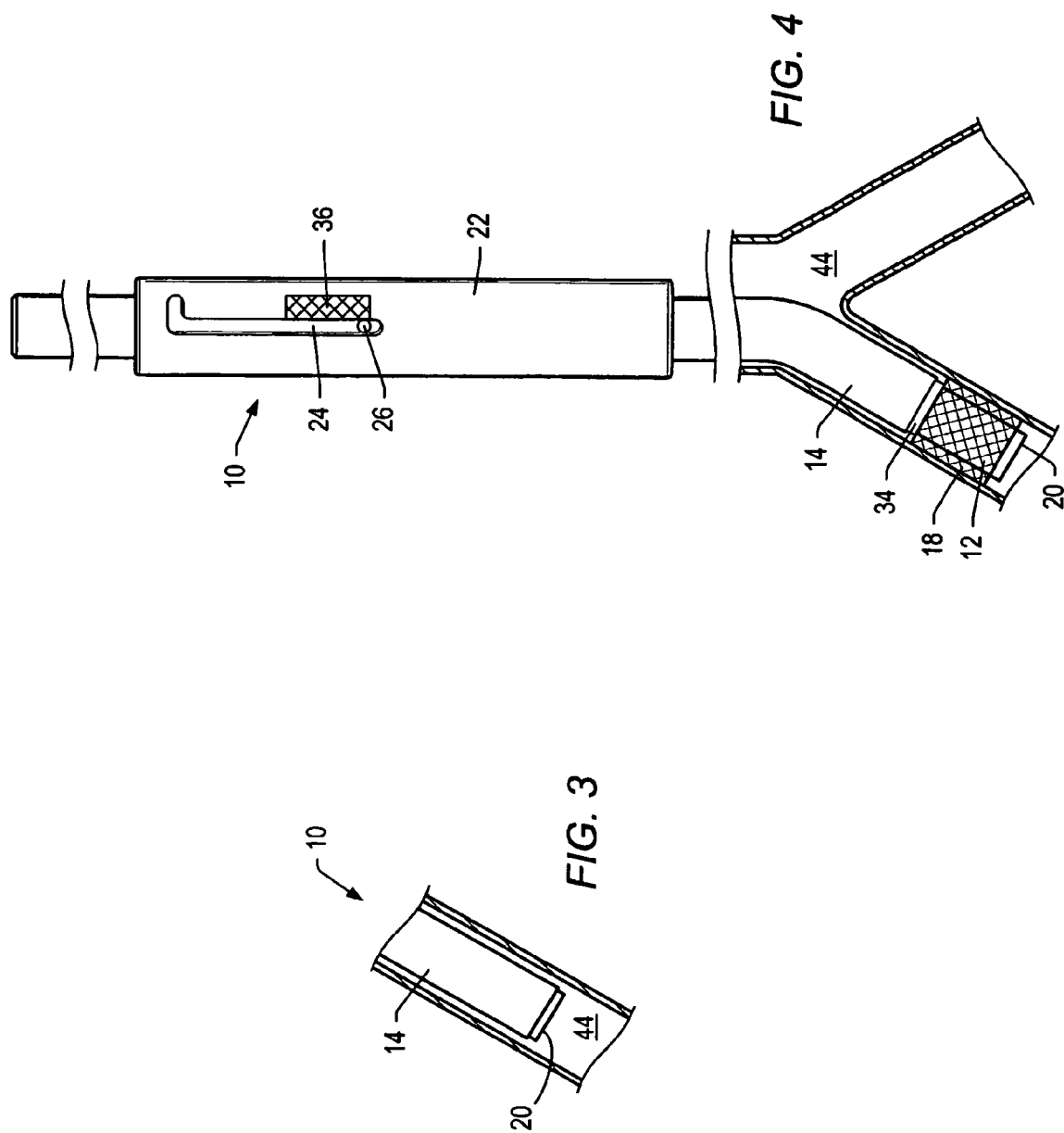

STENT DELIVERY SYSTEM AND METHOD OF USE

PRIORITY CLAIM

This application claims priority to PCT Patent Application No. PCT/US03/30844 entitled "STENT DELIVERY SYSTEM AND METHOD OF USE" filed on Sep. 30, 2003, which claims priority to Provisional Patent Application No. 60/414,770 entitled "STENT DELIVERY SYSTEM" filed on Sep. 30, 2002.

BACKGROUND OF THE INVENTION

1. Field of the Invention

The present invention relates to stent deployment devices and methods for deploying stents. Embodiments of the invention relate to a system that provides for deploying a stent using an endoscope.

2. Description of the Related Art

Endoscopes are effective devices for diagnosing and treating patients with minimal intervention and discomfort and are often used to explore and perform biopsies in such areas as the alimentary tract. In general, an endoscope has a flexible elongated tubular body equipped with a miniature television camera or other viewing device, a light, and a working lumen or channel. The working channel is used to store and deploy a variety of surgical tools for different endoscopic operations.

A stent is a resilient device often used in anchoring vascular grafts and for supporting body openings during the grafting of vessels and tubes of the body during surgery. Also, stents are frequently used, without grafts, for supporting luminal patency. More recently, artificial (woven or non woven polymeric) grafts are used in cardiac, vascular, and nonvascular applications to provide extra support. Moreover, stents can be separated into self-expanding and plastically deformed stents. A self-expanding stent is deployed by its self-expanding resilience. A plastically deformed stent is deployed by plastic deformation of the constituent material with a balloon or other such dilating instrument.

Endoscopes are effectively utilized to deploy stents within a body cavity in a minimally invasive manner. In a conventional method, a stent is compressed to fit into the working channel of the endoscope and is delivered to the body cavity to be treated. However, storing a stent within the working channel of an endoscope causes several problems. First, there is a limitation on the size of the stent that can be compressed to fit in the working channel. Because the working channel of the endoscope is often relatively small, a large stent may not fit within the working channel. Thus, this method is not suitable for deploying large stents.

Additionally, fitting a stent in the working channel often results in deformation of the stent when it is deployed into the body cavity. Since stents are made of resilient material, compression within the working channel may cause the stent to become deformed and fail to return to its original shape when released from the working channel. The more the stent gets strained, the more the deformation is likely to be.

A specific example of the aforementioned problems can be seen when observing commonly used methods for positioning and deploying pulmonary stents. Currently, surgeons insert a bronchoscope into an air passageway of a patient to visually observe where a pulmonary stent needs to be positioned. They typically use a type of guide wire inserted through the bronchoscope to mark the position where they want to place the pulmonary stent. At this point, the bronchoscope is removed and a stent delivery system (typically associated with delivering vascular stents) is used to place the pulmonary stent using the guide wire and fluoroscopy or radioscopy to assist in positioning. This current technique requires several distinct and difficult steps and does not allow the surgeon to visually observe the actual placement of the stent. There is a need for a stent delivery system which allows for visual observation during placement of the stent and which requires fewer steps.

Consequently, there is a need for stent deployment systems and methods that provide a solution to the aforementioned problems and permit deployment of stents, regardless of size, into body cavities.

SUMMARY

A stent delivery system may be employed to position a stent within a body lumen. A stent delivery system may include a first conduit and a second conduit. The first and second conduit may be at least partially flexible. At least the first conduit may be formed from materials that inhibit collapse of the first conduit during use. An endoscope may be positionable in the first conduit. The endoscope may allow the operator of the stent delivery system to visually observe the placement and deployment of the stent. The stent may be positioned towards the distal end of the stent delivery system between the first and second conduits. Once in position, the second conduit may be retracted towards the proximal end of the stent delivery system exposing the stent.

A first conduit of a stent delivery system may be reinforced to provide structural strength and inhibit collapse of the first conduit. Reinforcement for the first conduit may include, but is not limited to, a spiral of structural material in a body of the first conduit, a ring or rings of structural material located in a body of the first conduit at a position or positions along a length of the first conduit. The structural material may include, but is not limited to, metal, a metallic alloy, polymers or combinations thereof. Portions of the first conduit may be flexible to allow the stent delivery system to conform to curves of a body lumen during insertion of the stent delivery system into the patient.

A second conduit of a stent delivery system may include an inner layer coupled to an outer layer. At least the outer layer of the second conduit may be coupled to a grip. The second conduit may be formed from materials that are at least partially flexible. The second conduit may be formed from materials that inhibit collapse of the second conduit under pressure.

A stent delivery system may include a lock. The lock may function to inhibit movement of the first conduit relative to the second conduit during use. The lock may include a clamp (e.g., a screw clamp). In some embodiments, the lock may include a grip, an opening, and a pin. The grip may be coupled to at least a portion of the proximal end of the second conduit. The grip may allow grasping of the stent delivery system. The first conduit may be positionable in the grip. The opening of the lock may extend at least partially through the grip. The pin of the lock may be coupled to the first conduit and positionable in the opening in the grip. The pin and opening may function in combination to limit longitudinal movement to within a specified range.

A stent delivery system may include indicia. At least a portion of the indicia may be visibly positioned on the proximal end of the stent delivery system. The indicia may function to assist the operator in determining an extent of deployment of the stent during a procedure.

A stent delivery system may include a stop. The stop may be positioned approximate the distal end of the stent delivery system between the first and second conduits. The stop may be coupled to the first conduit. The stop may function to inhibit movement of the stent in a proximal direction relative to the first conduit.

BRIEF DESCRIPTION OF THE DRAWINGS

Advantages of the present invention will become apparent to those skilled in the art with the benefit of the following detailed description of embodiments and upon reference to the accompanying drawings in which:

FIG. 3 depicts a cross sectional view of an embodiment of a portion of a stent delivery system during deployment of a stent in a body lumen.

FIG. 4 depicts a cross sectional view of an embodiment of a portion of a stent delivery system after deployment of a stent in a body lumen.

Figure 1:
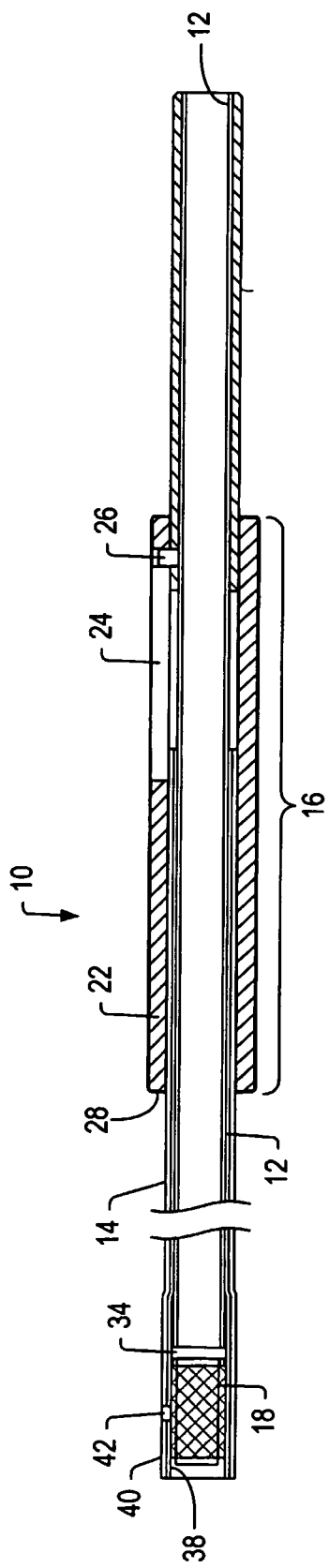
FIG. 1 depicts a cross sectional view of an embodiment of a stent delivery system.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Figure 2:
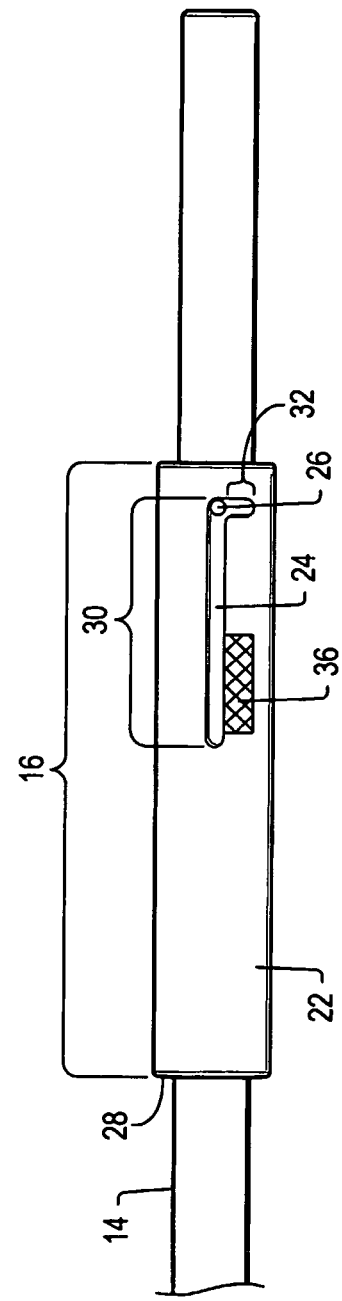
FIG. 2 depicts a side view of an embodiment of a proximal end of a stent delivery system.

Referring to the drawings, and particularly to FIGS. 1-2, a stent delivery system is designated generally by reference number 10. Stent delivery system 10 may be used in a procedure that requires placement of a stent within a body lumen of a patient. Stent delivery system 10 may be used to deliver a stent under direct observation using an endoscope in combination with stent delivery system 10. Examples of surgical procedures include, but are not limited to, placement of a pulmonary stent in an air passageway using stent delivery system 10 in combination with a bronchoscope.

Stent delivery system 10 may be formed from various materials. The materials may include, but are not limited to, metals, metal alloys, polymers, ceramics, and combinations thereof. Some stent delivery systems may include components made of materials that can be autoclaved and/or chemically sterilized. Some stent delivery systems may include components that are provided in a sterile condition. Sterilized and/or sterile components may be assembled together to form a stent delivery system. In some embodiments, an entire stent delivery system may be made of materials that can be autoclaved and/or chemically sterilized so that the stent delivery system is a reusable instrument. In other stent delivery systems, all or selected components of the stent delivery system may be made of sterile, disposable materials so that all or components of the stent delivery system are designed for single use.

FIGS. 1 and 2 depict cross sectional and side views of an embodiment of a stent delivery system. Some embodiments of stent delivery system 10 may include first conduit 12, second conduit 14, and lock 16. First conduit 12 may be positionable in second conduit 14. Lock 16 may function to inhibit movement of second conduit 14 relative to first conduit 12. In some embodiments, lock 16 may function to limit movement of second conduit 14 relative to first conduit 12 to within a specified range. Stent delivery system 10 may be used in combination with stent 18 and endoscope 20 (not pictured in FIGS. 1 and 2). Stent 18 may be positioned in between the distal ends of first conduit 12 and second conduit 14. Endoscope 20 may be positionable in first conduit 12. Stent 18 may be deployed in a body lumen by retracting second conduit 14 relative to first conduit 12 (as depicted in FIGS. 3 and 4).

Stent 18 may include any one of commonly available stents known to someone skilled in the art, which is inserted into a vessel or passage to keep the lumen open and prevent closure due to a stricture or external compression. Stent 18 may include, but is not limited to, pulmonary or vascular stents. Stent delivery system 10 may be used in combination with stents which are deployed in various ways, including self-expanding stents and balloon expandable stents.

Endoscope 20 (depicted in FIG. 3) may include any flexible or semi-flexible instrument configured to be inserted into a body lumen. Endoscope 20 may include some type of direct visualization system (e.g., a fiber-optic camera system). In some embodiments, endoscope 20 may be formed from a more rigid substance. The use of a rigid or flexible endoscope is determined by the surgeon based on the body lumen the endoscope is to be inserted into. One example of an endoscope 20 that may be used is a bronchoscope.

In some embodiments, lock 16 may include grip 22, opening 24, and pin 26. Grip 22 may function as a surface for a user (e.g., a surgeon) to grasp. Distal end 28 of grip 22 may be coupled to second conduit 14. In some embodiments, grip 22 may be considered a less flexible extension of second conduit 14. Grip 22 may include surface deformations, patterning, chemical treatment, or surface coatings to increase the coefficient of friction and decrease the risk of a user's hand from slipping from grip 22 during use. When in an "unlocked" position, grip 22 facilitates retraction of second conduit 14 relative to first conduit 12 during use. Opening 24 may extend through grip 22. Opening 24 may be an elongated "L" shape as depicted in FIG. 2. Pin 26 may be coupled to first conduit 12. Pin 26 may extend into at least a portion of opening 24. First portion 30 of opening 24, in grip 22, in combination with pin 26 may function to limit the longitudinal range of motion of second conduit 14 relative to first conduit 12. In certain embodiments, the length of first portion 30 may be such that when pin 26 has traveled the entire length of first portion 30 upon retraction, stent 18 may be fully deployed. Second portion 32 of opening 24, in grip 22, in combination with pin 26 may function to inhibit longitudinal motion of second conduit 14 relative to first conduit 12. When pin 26 is positioned in second portion 32 of opening 24 this may be loosely referred to as a "locked"

position. When pin 26 is in a locked position, second conduit 14 is inhibited from longitudinal motion relative to first conduit 12. When pin 26 is positioned in first portion 30 of opening 24 this may be loosely referred to as an "unlocked" position. When pin 26 is in an unlocked position, second conduit 14 is allowed longitudinal motion relative to first conduit 12 (the extent of longitudinal motion is however limited by the length of first portion 30). Lock 16 may function such that a user needs only one hand to lock and/or unlock lock 16, thereby freeing a user's other hand for other tasks.

Figure 5:
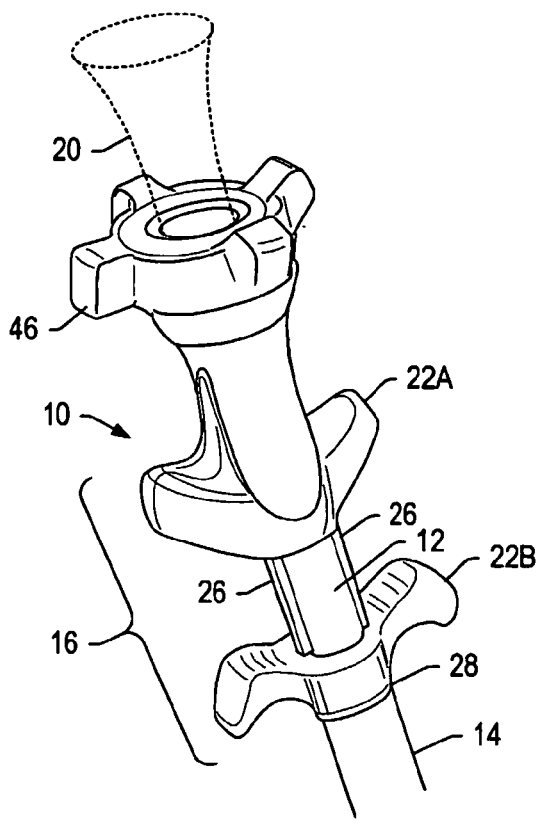
FIG. 5 depicts a perspective view of an embodiment of a proximal end of a stent delivery system.
Figure 6:
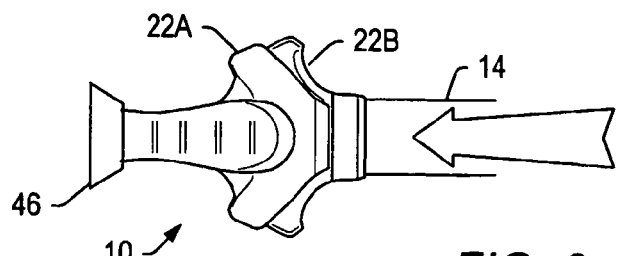
FIG. 6 depicts a side view of an embodiment of a proximal end of a stent delivery system wherein a second conduit is in a retracted position relative to a first conduit.
Figure 7:
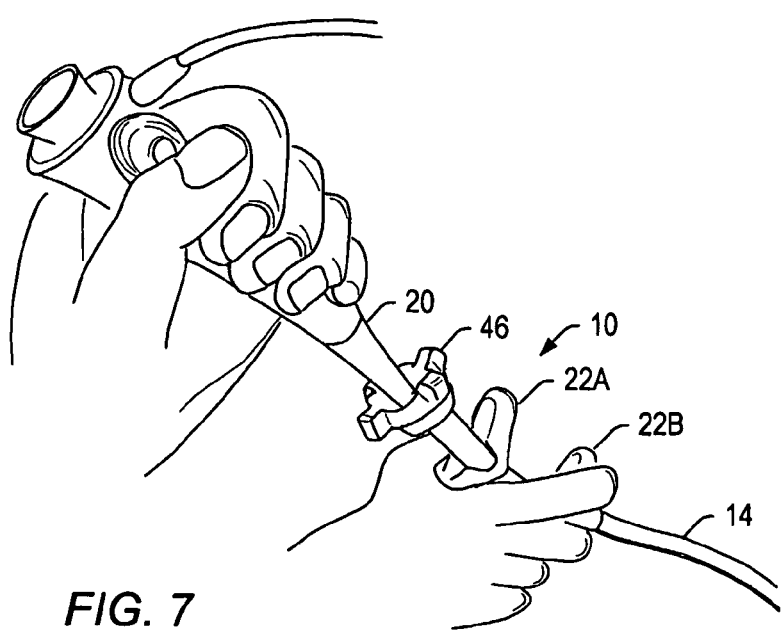
FIG. 7 depicts a perspective view of an embodiment of a proximal end of a stent delivery system during use wherein an endoscope is positioned in a first conduit.

In certain embodiments, lock 16 may include first grip 22A, second grip 22B, and pins 26 as depicted in FIGS. 5-7. Grips 22A, B may function as a surface for a user (e.g., a surgeon) to grasp. Distal end 28 of second grip 22B may be coupled to second conduit 14. In some embodiments, grips 22A, B may be considered a less flexible extension of second conduit 14. Grips 22A, B may include surface deformations, patterning, chemical treatment, or surface coatings to increase the coefficient of friction and decrease the risk of a user's hand from slipping from grips 22A, B during use. Lock 16 may function to limit movement of second conduit 14 relative to first conduit 12 to within a specified range. Second conduit 14 may be retracted when a user grasps both first grip 22A and second grip 22B concurrently. Upon grasping both first grip 22A and second grip 22B, the user may slide second grip 22B over first conduit 12 toward first grip 22A retracting second conduit 14. Retracting second conduit 14 potentially exposes at least a portion or all of stent 18. Second grip 22B may be configured to travel within a specified range along first conduit 12. First grip 22A may function as a stop, inhibiting second grip 22B from traveling beyond a distal end of first grip 22A.

Figure 8:
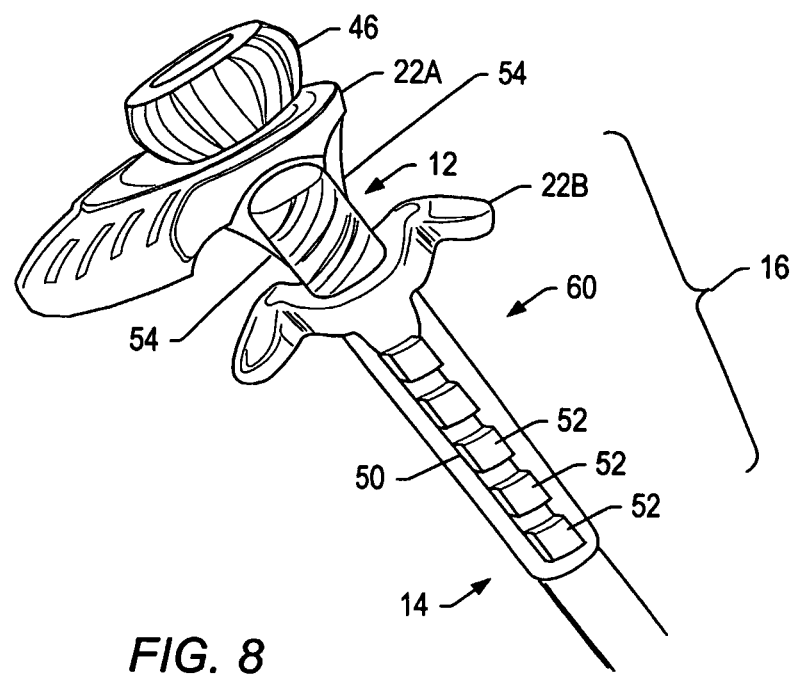
FIG. 8 depicts a perspective view of an embodiment of a proximal end of a stent delivery system including a ratcheted stop and/or lock.
Figure 9:
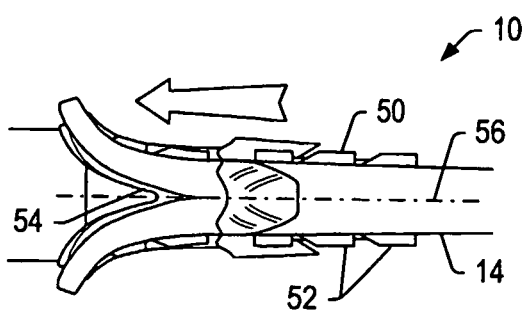
FIG. 9 depicts a side view of an embodiment of a proximal end of a ratcheted stop and/or lock mechanism of a stent delivery system during use.

In some embodiments, lock 16 may include first grip 22A, second grip 22B, and a ratchet locking system 48. Ratchet locking system 48 may include a ratchet guide 50 as depicted in FIGS. 8-9. Ratchet guide 50 may include ratchet guide stops 52. Ratchet guide 50 may include any number of ratchet guide stops 52. A number of ratchet guide stops 52 may be dependent on a desired range of movement of second conduit 14 relative to first conduit 12. A size of ratchet guide stops 52 may be dependent on a desired increment of movement per ratchet guide stop. Sizes of ratchet guide stops 52 may vary so as to allow smaller more controlled increments of movement of second grip 22B (and consequently second conduit 14) relative to first conduit 12 at different times during deployment of stent 18. Ratchet guide 50 may be coupled to second conduit 14. Ratchet guide 50 may be formed as a portion of second conduit 14. Ratchet locking system 48 may allow stent 18 to be deployed in two or more steps. Steps for deployment of stent 18 may include moving second grip 22B over one or more ratchet guide stops 52 toward the distal end of stent delivery system 10 and then subsequently pulling back second grip 22B toward the proximal end of stent delivery system 10. Due to the fact ratchet guide stops 52 are coupled to second conduit 14, as second grip 22B is pulled back toward the proximal end of stent delivery system 10 second conduit 14 is also retracted. At least one advantage of ratchet locking system 48 may include allowing a multiple step controlled deployment of stent 18. Multiple step controlled deployment of stent 18 may facilitate users of the system with smaller hands to grasp and use stent delivery system 10 with only one hand.

As second conduit 14 is retracted using ratchet locking system 48 the proximal end of second conduit 14 may begin to abut against the distal end of first grip 22A. In some embodiments, a pliable material forming second conduit 14 may "bunch up" or "gather" around the distal end of first grip 22A to relieve the pressure of the abutment of the proximal end of second conduit 14 against the distal end of first grip 22A. In certain embodiments, the distal end of first grip 22A may include separator 54. Embodiments of separator 54 are depicted in FIGS. 8 and 9. Separator 54 may include an edge sharp enough to split or cut second conduit 14 on one or more sides. Separator 54 may be designed to direct cut portions of second conduit 14 away from the distal end of first grip 22A as depicted in FIG. 9. Cutting and directing cut portions of second conduit 14 away from the distal end of first grip 22A as the proximal end of second conduit 14 moves toward the distal end of first grip 22A may relieve the pressure of the abutment of the proximal end of second conduit 14 against the distal end of first grip 22A. In some embodiments, second conduit 14 may include a line of detachment 56. The line of detachment may facilitate cutting away second conduit 14 during use. The line of detachment may extend the majority or all of the length of second conduit 14. The line of detachment may extend along a short portion of the length of second conduit 14. The line of detachment may be perforated. The line of detachment may be scored.

In some embodiments, a lock may include any device, system, or mechanism which may limit and/or inhibit movement of second conduit 14 relative to first conduit 12. There are many such devices known to one skilled in the art, including for example, screw clamps, snapper clamps, and oeticker clamps.

In some embodiments, a proximal end of second grip 22B may be formed into a shape complementary to a distal end of first grip 22A (as depicted in FIGS. 5-8). Forming portions of first grip 22A and second grip 22B so as to be complementary to one another may facilitate the use of stent delivery system 10 allowing retraction of second conduit 14 with lock 16 to be performed by a user using only one hand (as depicted in FIG. 7). Portions of first grip 22A and second grip 22B may be formed as depicted in FIGS. 5-7 to fit a user's hand facilitating use of stent delivery system 10. Pins 26 may be coupled to first conduit 12 and/or formed as part of first conduit 12. An inner surface of second grip 22B may be "keyed" or formed to slide over first conduit 12 including pins 26; however, pins 26 may assist in keeping at least portions of first conduit 12 and second conduit 14 in a specific orientation relative to one another. Pins 26 may inhibit first conduit 12 and second conduit 14 from "twisting" relative to one another.

In some embodiments, lock 16 may function to limit movement of second conduit 14 relative to first conduit 12 to within a specified range. In keeping with this function, lock 16 may include a second stop. This second stop may function to inhibit movement of second grip 22B (and consequently second conduit 14) relative to first conduit 12 in a direction toward the distal end of stent delivery system 10.

In certain embodiments, stent delivery system 10 may include a second lock 46. Examples of second lock 46 are depicted in FIGS. 5, 7, and 8. Second lock 46 may function to inhibit movement of endoscope 20 relative to first conduit 12 during use. Upon positioning second lock 46 in a proximal end of first conduit 12, second lock 46 may be engaged at an appropriate time inhibiting further movement of endoscope 20 relative to first conduit 12.

In some embodiments, stent delivery system 10 may include stop 34 depicted in FIGS. 1 and 3. Stop 34 may be a ring coupled to the outer surface of first conduit 12. Stop 34 may be positioned towards the distal end of first conduit 12, substantially adjacent to the proximal end of stent 18 during use. Stop 34 may function to inhibit movement of stent 18 in a direction towards the proximal end of stent delivery system 10. Stop 34 may insure that when second conduit 14 is retracted to deploy stent 18, stent 18 may not be retracted with second conduit 14 due to frictional forces between the adjoining surfaces of stent 18 and second conduit 14. In addition, stop 34 may include a radius edge on the proximal end to reduce wear on second conduit 14. Stop 34 may include a substantially flat surface on the distal end for the proximal end of stent 18 to abut against to more effectively inhibit movement of stent 18 past stop 34. Stop 34 may comprise polymers, metals, and/or ceramics.

Some stent delivery system embodiments may include indicia 36 as depicted in FIGS. 2 and 3. Indicia 36 may be positioned on the proximal end of stent delivery system 10. At least a portion of indicia 36 may be visible during use. Indicia 36 may function to assist a user of stent delivery system 10 to determine a stage of deployment for stent 18. For example, indicia 36 may indicate to the user when stent 18 has been fully deployed and/or at least partially deployed. Indicia 36 may include many different forms indicating different stages of deployment, for example, different colored bands (such as red and green), numbers, and/or hash marks. In some embodiments, indicia 36 may be adjacent opening 24 in grip 22, so the position of pin 26 relative to indicia 36 may assist a user in determining a deployment stage of stent 18. Indicia 36 may be formed in a variety of ways known to someone skilled in the art.

As previously mentioned, stents employed in combination with stent delivery system 10 may include self-expanding stents and balloon expandable stents. In theory, self-expanding stents once fully deployed, by for example retracting the distal end of second conduit 14 beyond the proximal end of stent 18, will expand and lock in place in the body lumen where placed by stent delivery system 10. Balloon expandable stents, however, once deployed must have pressure applied to their inner surface to force the balloon expandable stent to expand and lock in place. In some embodiments, once stent 18 has been deployed, a balloon catheter may be inserted into the body lumen and into stent 18. The balloon may be inflated once appropriately positioned in stent 18. Inflating the balloon of the balloon catheter may provide the necessary force to expand and lock in place stent 18 (wherein stent 18 is a balloon expandable stent or similar device). The balloon catheter may be inserted into the body lumen after stent delivery system 10 has been removed. In an alternative embodiment, the balloon catheter may be inserted through stent delivery system 10, using stent delivery system 10 as a guide. The balloon catheter may be inserted through endoscope 20 or through first conduit 12 after removal of endoscope 20. In some embodiments, a balloon or inflation member may be coupled to the outer surface of the distal end of first conduit 12. An inflation conduit may be coupled to the inflation member. The inflation conduit may transport a fluid (e.g., air) into the inflation member. In some embodiments, an inflation member and/or an inflation conduit, as described, may be formed in the walls of first conduit 12. The fluid may be supplied from an inflator. The inflator may be, but is not limited to, a bellows, a pump, or a fluid supply. After inflation, a valve may be turned, or constant pressure may be applied to the inflation member, to inhibit flow of fluid out of the inflation member. To deflate the inflation member, a valve may be turned, or pressure applied to inflation member may be shut off, to allow fluid to flow out of the inflation member. In some embodiments, the inflator may operate in a first way to allow fluid to be inserted into the inflation member. The inflator may operate in a second way to allow fluid to be removed from the inflation member. In some expandable member embodiments, an inflator may be attached to inflation conduit to fill expandable member. The inflator may be removed from the inflation conduit to allow the inflation member to be deflated. In some embodiments, a deflator may be attached to the inflation conduit to remove fluid from the inflation member to deflate the inflation member. If necessary, an inflation system, as described herein, may be used in combination with stents other than balloon expandable stents.

In some embodiments, a balloon or inflation member may be coupled to the outer surface of the distal end of second conduit 14. An inflation conduit may be coupled to the inflation member. The inflation conduit may transport a fluid (e.g., air) into the inflation member. In some embodiments an inflation member and/or an inflation conduit, as described, may be formed in the walls of second conduit 14. The fluid may be supplied from an inflator as described herein above. The inflation member may function to perform an angioplasty procedure. The angioplasty procedure may function to enlarge the cross-sectional area of obstructed body lumens and, consequently, to increase the flow of fluids (e.g., air and/or blood) in the body lumen. Angioplasty may be performed before retracting second conduit 14 and deploying stent 18. In addition, the inflatable member may function to substantially seal off the body lumen if necessary.

First conduit 12 may be made of a material or materials that allow a portion of the first conduit to be flexible. A flexible first conduit may facilitate insertion of stent delivery system 10 into a patient's air passage. First conduit 12 may be formed from a material which inhibits collapse of first conduit 12. A portion of first conduit 12 may include reinforcements that inhibit collapse of the first conduit. Reinforcements may be, but are not limited to, a spiral of reinforcing material, rings of reinforcing material, or combinations thereof. The reinforcing material may be, but is not limited to, metallic wire, polymer strands, and/or polymer and wire combinations. Reinforcements may inhibit collapse of first conduit 12 while allowing for some flexibility of the first conduit. Reinforcements may inhibit collapse of the patient's air passage during a surgical procedure. This may allow endoscope 20 to be removed from first conduit 12 once stent delivery system 10 is positioned within the body lumen. Removal of endoscope 20 during use may allow a patient to be ventilated through stent delivery system 10 when stent delivery system 10 is inserted in an air passageway. Stent delivery system 10 may be coupled to and/or used in combination with an endotracheal tube, a conventional ventilation system, and/or a jet ventilation system. In some stent delivery system embodiments, ventilation at a pressure between about 30 pounds per square inch (psi) and about 50 psi, with a volume between about 800 cc and about 1000 cc of oxygen, may be provided through first conduit 12. In some embodiments, first conduit 12 may be made of materials able to withstand over 100 psi.

A portion of first conduit 12 may include a layer or coating of a material on an inner surface that facilitates insertion of instruments into the first conduit. For example, the inner surface of first conduit 12 may include a fluorine containing resin layer (e.g., TEFLON®) or other material with a low coefficient of friction.

Portions of second conduit 14 may be flexible to facilitate insertion of stent delivery system 10 into a body lumen of a patient. An outer surface of second conduit 14 may include a layer or coating of a material having a low coefficient of friction to facilitate insertion of the second conduit into the body lumen.

In some embodiments, second conduit 14 may include inner layer 38 coupled to outer layer 40. Inner layer 38 may be coupled to outer layer 40 in any way known to one skilled in the art. In certain embodiments, an opening may be formed in inner layer 38 and outer layer 40. Plug 42 may be inserted or formed in the opening to couple inner layer 38 to outer layer 40. Inner layer 38 and outer layer 40 may be formed of different materials to take advantage of different properties that may be advantageous for outer and inner surfaces of second conduit 14.

A portion of stent delivery system 10 may be sized to fit within an air passage of a patient. A cylindrical first conduit may have a diameter between about 3 mm and about 20 mm. In some embodiments, the diameter may be between about 10 mm and about 17 mm. Larger or smaller diameters may be used to accommodate specific requirements for a particular patient.

FIG. 3 depicts a cross sectional view of an embodiment of a portion of stent delivery system 10 during deployment of stent 18 in body lumen 44. Body lumen 44 depicted in FIG. 3 may be an air passageway. At least a portion of stent delivery system 10 may be positioned in body lumen 44. Endoscope 20 may be positioned in first conduit 12 prior to, or after insertion of stent delivery system 10 in body lumen 44. Endoscope 20 may include a visualization system allowing an operator direct visualization of body lumen 44 to facilitate proper placement of the distal end of stent delivery system 10 and stent 18 without the use of fluoroscopy or radioscopy. Upon properly positioning stent 18 the operator may choose to remove endoscope 20 if the operator deems it advisable to ventilate the patient. Once endoscope 20 has been removed a ventilator may be coupled to the proximal end of first conduit 12. The ability to remove endoscope 20 during a procedure is an advantage resulting directly from forming first conduit 12 from materials resistant to collapsing. The operator may also choose to allow endoscope 20 to remain in first conduit 12 for the remainder of the procedure to allow the operator to continue visually observing the deployment of stent 18.

Upon properly positioning stent 18, lock 16 may be unlocked by rotating grip 22 such that pin 26 moves from second portion 32 of opening 24 to first portion 30 of opening 24. Once lock 16 is unlocked, grip 22 may be used to retract second conduit 14 toward the proximal end of stent delivery system 10 and the operator. Indicia 36 may indicate to the operator when second conduit 14 has been retracted enough to fully expose, and therefore deploy, stent 18 (as depicted in FIG. 4). FIG. 4 depicts a cross sectional view of an embodiment of a portion of stent delivery system 10 after deployment of stent 18 in body lumen 44.

Upon deployment, a self-expanding stent will expand and lock in position within body lumen 44, other types of stents (such as balloon expandable stents) may require further manipulation at this point as described herein. Stent delivery system 10 may be removed from body lumen 44.

In some embodiments, a pulmonary stent delivery system may comprise: a first conduit; and a second conduit, wherein the first conduit is positionable in the second conduit, and wherein the first and second conduits are configurable to releasably position a stent in a body lumen during use.

In some embodiments, a pulmonary stent delivery system may comprise: a first conduit; and a second conduit, wherein the first conduit is positionable in the second conduit.

Further modifications and alternative embodiments of various aspects of the invention will be apparent to those skilled in the art in view of this description. Airway assemblies may be modified to operate in other areas of a patient in which it is desired to separate a first region from a second region by a seal formed in a passage of the patient. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A pulmonary stent delivery system comprising:
a first conduit, wherein at least a portion of a bronchoscope is positionable in the first conduit during use of the stent delivery system, and wherein the first conduit has a diameter of between 3 mm and 20 mm and is sized to allow a bronchoscope to move distally and proximally through the first conduit;
a second conduit, wherein at least a portion of the first conduit is positionable in the second conduit, wherein the second conduit is configured to contain at least a portion of a pulmonary stent, wherein the stent comprises a distal portion terminating at a distal end and a proximal portion terminating at a proximal end, wherein the second conduit is movably positionable with respect to the first conduit, and wherein a distal end of the second conduit is movable in a direction toward a proximal end of the first conduit to expose at least a portion of the distal end of the stent during use;
a stop coupled to, and protruding outwardly from, the outer surface of the first conduit and positioned approximate to the proximal end of the stent when the stent is positioned between the first and second conduits, wherein the stop is configured to abut against the proximal end of the stent to inhibit movement of the stent in a proximal direction relative to the first conduit;
a bronchoscope that is positioned within the first conduit such that a distal end of the bronchoscope is extendable adjacent to a distal end of the first conduit, the second conduit or the stent;
a first grip coupled to the first conduit, the first grip including a user-engagement portion extending radially away from a longitudinal axis of the first conduit; and
a second grip coupled to the second conduit, the second grip including a user engagement portion that comprises a first finger grip that is configured to receive a user's index finger and a second finger grip that is configured to receive a user's middle finger, wherein the first finger grip extends radially away from a longitudinal axis of the second conduit in a first direction and the second finger grip extends away from the longitudinal axis of the second conduit in a second direction that is opposite of the first direction, wherein the first and second grips are configured to facilitate one-handed retraction of the second conduit to deploy the stent as the user retracts the second grip proximally toward the first grip;

wherein the first conduit and the second conduit are sized to permit positioning of the stent between an outer surface of the first conduit and an inner surface of the second conduit, thereby allowing extension of the bronchoscope through the first conduit and the stent.

2. The stent delivery system of claim 1, further comprising:
a first lock configurable to inhibit movement of the first conduit relative to the second conduit during use; and
a second lock configurable to inhibit movement of the bronchoscope relative to the first conduit during use.

3. The stent delivery system of claim 1, further comprising a lock configurable to inhibit movement of the first conduit relative to the second conduit during use, wherein the lock comprises:
the first grip; and
the second grip;
wherein at least a portion of the first grip is configurable to inhibit movement of the second grip in a direction toward a proximal end of the stent delivery system beyond the portion of the first grip.

4. The stent delivery system of claim 1, further comprising a lock configurable to inhibit movement of the first conduit relative to the second conduit during use, wherein the lock comprises:
the first grip;
the second grip; and
one or more pins coupled to the first conduit, wherein at least one of the pins is configurable to inhibit portions of the first and second conduits from moving transversely to each other;
wherein at least a portion of the first grip is configurable to inhibit movement of the second grip in a direction toward a proximal end of the stent delivery system beyond the portion of the first grip.

5. The stent delivery system of claim 1, further comprising a lock configurable to inhibit movement of the first conduit relative to the second conduit during use, wherein the lock comprises a clamp.

6. The stent delivery system of claim 1, wherein at least a portion of the first conduit is partially flexible.

7. The stent delivery system of claim 1, wherein at least a portion of the second conduit is partially flexible.

8. The stent delivery system of claim 1, wherein at least a portion of the second conduit is configured to inhibit collapse of the second conduit.

9. The stent delivery system of claim 1, wherein the first conduit comprises a polymer.

10. The stent delivery system of claim 1, wherein the second conduit comprises a polymer.

11. The pulmonary stent delivery system of claim 1, further comprising:
a stent disposed between an outer surface of the first conduit and an inner surface of the second conduit, wherein the stent comprises a distal portion terminating at a distal end and a proximal portion terminating at a proximal end,
wherein the second conduit is configured to contain substantially all of the stent between the outer surface of the first conduit and the inner surface of the second conduit.

12. The stent delivery system of claim 1, wherein the second conduit is configured to retract in a proximal direction relative to the first conduit such that the distal end of the stent travels out of a distal opening in the distal end of the second conduit.

13. The stent delivery system of claim 1, wherein the distal end of the second conduit is movable in a direction toward the proximal end of the first conduit to expose a given portion of the stent after all more distal portions of the stent have been exposed.

14. The stent delivery system of claim 1, wherein the second conduit is configured to contain the entirety of the stent between an outer surface of the first conduit and an inner surface of the second conduit.

15. The stent delivery system of claim 1, wherein the stop comprises a radius edge.

16. The stent delivery system of claim 1, wherein the first conduit is positionable, with respect to the stent, such that the distal end of the first conduit is positionable flush with the distal end of the stent.

17. The stent delivery system of claim 1, wherein the first conduit comprises spiral reinforcing in the first conduit which inhibits collapse of the first conduit under the stent when the stent is positioned on the first conduit.

18. The stent delivery system of claim 1, wherein the first conduit has a diameter of between about 10 mm and about 17 mm.

19. The stent delivery system of claim 1, wherein
the user-engagement portion of the first grip is shaped to receive a user's hand between a thumb and index finger.

20. A pulmonary stent delivery system comprising:
a first conduit, wherein at least a portion of a bronchoscope is positionable in the first conduit during use of the stent delivery system, and wherein the first conduit has a diameter of between 3 mm and 20 mm and is sized to allow a bronchoscope to move distally and proximally through the first conduit;
a second conduit, wherein at least a portion of the first conduit is positionable in the second conduit, wherein the second conduit is configured to contain at least a portion of a pulmonary stent, wherein the stent comprises a distal portion terminating at a distal end and a proximal portion terminating at a proximal end, and wherein the second conduit is movably positionable with respect to the first conduit, and wherein the distal end of the stent is exposed prior to exposure of other portions of the stent upon movement of the second conduit in a proximal direction relative to the first conduit;
a stop coupled to, and protruding outwardly from, the outer surface of the first conduit and positioned approximate to the proximal end of the stent between the first and second conduits, wherein the stop is configured to abut against the proximal end of the stent to inhibit movement of the stent in a proximal direction relative to the first conduit; and
a bronchoscope that is positioned within the first conduit such that a distal end of the bronchoscope is extendable adjacent to a distal end of the first conduit, the second conduit or the stent;
wherein the first conduit and the second conduit are sized to permit positioning of the stent between an outer surface of the first conduit and an inner surface of the second conduit, thereby allowing extension of the bronchoscope through the first conduit and the stent.

21. The stent delivery system of claim 20, wherein the distal end of the second conduit is movable in a direction toward a proximal end of the first conduit to expose a portion of the stent after all more distal portions of the stent have been exposed.

22. The stent delivery system of claim 20, wherein the second conduit is configured to contain the entirety of the stent between an outer surface of the first conduit and an inner surface of the second conduit.

23. The stent delivery system of claim 20, wherein the second conduit comprises an inner layer coupled to an outer layer, the inner layer and outer layer being formed of different materials.

24. A method for positioning a pulmonary stent, comprising:
obtaining a pulmonary stent delivery system, comprising:
a first conduit, wherein at least a portion of a bronchoscope is positionable in the first conduit during use of the stent delivery system, and wherein the first conduit has a diameter of between 3 mm and 20 mm and is sized to allow a bronchoscope to move distally and proximally through the first conduit;
a second conduit, wherein at least a portion of the first conduit is positionable in the second conduit, wherein the second conduit is configured to contain at least a portion of a pulmonary stent, wherein the stent comprises a distal portion terminating at a distal end and a proximal portion terminating at a proximal end, wherein the second conduit is movably positionable with respect to the first conduit, and wherein a distal end of the second conduit is movable in a direction toward a proximal end of the first conduit to expose at least a portion of the distal end of the stent during use;
a stop coupled to, and protruding outwardly from, the outer surface of the first conduit and positioned approximate to the proximal end of the stent when the stent is positioned between the first and second conduits, wherein the stop is configured to abut against the proximal end of the stent to inhibit movement of the stent in a proximal direction relative to the first conduit;
a bronchoscope that is positioned within the first conduit such that a distal end of the bronchoscope is extendable adjacent to a distal end of the first conduit, the second conduit or the stent; wherein the first conduit and the second conduit are sized to permit positioning of the stent between an outer surface of the first conduit and an inner surface of the second conduit, thereby allowing extension of the bronchoscope through the first conduit and the stent;
a first grip coupled to the first conduit, the first grip including a user-engagement portion extending radially away from a longitudinal axis of the first conduit; and
a second grip coupled to the second conduit, the second grip including a user engagement portion that comprises a first finger grip that is configured to receive a user's index finger and a second finger grip that is configured to receive a user's middle finger, wherein the first finger grip extends radially away from a longitudinal axis of the second conduit in a first direction and the second finger grip extends away from the longitudinal axis of the second conduit in a second direction that is opposite of the first direction, wherein the first and second grips are configured to facilitate one-handed retraction of the second conduit to deploy the stent as the user retracts the second grip proximally toward the first grip;
positioning the pulmonary stent delivery system in a patient;
positioning the bronchoscope in the first conduit of the pulmonary stent delivery system; and
deploying the stent.

25. The method of claim 24, wherein positioning the pulmonary stent delivery system comprises positioning a distal end of the pulmonary stent delivery system in an air passageway of a patient.

26. The method of claim 24, wherein positioning the bronchoscope comprises positioning the bronchoscope through the first conduit such that a distal end of the bronchoscope is adjacent to a distal end of the pulmonary stent delivery system so that a stent deployment site is visually observable through the bronchoscope.

27. The method of claim 24, wherein deploying the stent comprises retracting the second conduit relative to the first conduit to deploy the stent.

28. The method of claim 24, further comprising:
receiving the user-engagement portion of the first grip between a thumb and index finger of the user;
receiving the user-engagement portion of the second grip with a user's index and middle fingers;
retracting the second grip proximally toward the first grip with one hand such that the second grip comes into abutment with the first grip, such that retracting the second grip retracts the second conduit to deploy the stent.

* * * * *